United States Patent
Marshall

(10) Patent No.: US 11,229,667 B2
(45) Date of Patent: *Jan. 25, 2022

(54) MAGNESIUM/LITHIUM PREPARATIONS FOR NEUROPROTECTION AND NEUROTROPHIC BENEFITS

(71) Applicant: FP Nutraceuticals, LLC, Sante Fe Springs, CA (US)

(72) Inventor: Timothy M. Marshall, Tucson, AZ (US)

(73) Assignee: FP Nutraceuticals, LLC, Santa Fe Springs, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/471,519

(22) PCT Filed: Feb. 18, 2019

(86) PCT No.: PCT/US2019/018414
§ 371 (c)(1),
(2) Date: Jun. 19, 2019

(87) PCT Pub. No.: WO2019/161331
PCT Pub. Date: Aug. 22, 2019

(65) Prior Publication Data
US 2020/0384015 A1 Dec. 10, 2020

Related U.S. Application Data

(60) Provisional application No. 62/632,043, filed on Feb. 19, 2018.

(51) Int. Cl.
*A61K 33/06* (2006.01)
*A61K 33/00* (2006.01)
*A61K 45/06* (2006.01)
*A61K 9/00* (2006.01)

(52) U.S. Cl.
CPC ............ *A61K 33/06* (2013.01); *A61K 9/0053* (2013.01); *A61K 9/0056* (2013.01); *A61K 33/00* (2013.01); *A61K 45/06* (2013.01)

(58) Field of Classification Search
CPC .... A61K 33/06; A61K 9/0053; A61K 9/0056; A61K 33/00; A61K 45/06
See application file for complete search history.

(56) References Cited

U.S. PATENT DOCUMENTS

| | | |
|---|---|---|
| 6,174,890 B1 | 1/2001 | Riga et al. |
| 2006/0078629 A1 | 4/2006 | Serfontein |
| 2007/0048416 A1* | 3/2007 | Uzunian .................. A23L 5/42 426/250 |
| 2007/0190209 A1* | 8/2007 | Sinnott .................. A61K 36/88 426/72 |
| 2011/0014277 A1* | 1/2011 | Bieley .................. A61K 31/375 424/450 |
| 2013/0123355 A1 | 5/2013 | Chopra |
| 2013/0309291 A1* | 11/2013 | Stoll ........................ A23G 3/36 424/440 |
| 2015/0209306 A1 | 7/2015 | Bredesen et al. |
| 2015/0265665 A1* | 9/2015 | Moshtagh ................ A23G 3/48 424/777 |

OTHER PUBLICATIONS

Comalada, M., et al., "In vivo quercitrin anti-inflammatory effect involves release of quercetin, which inhibits inflammation through down-regulation of the NF-kB pathway," European Journal of Immunology 35.2: 584-592, Jan. 28, 2005.
International Search Report and Written Opinion issued in related International Application No. PCT/US2019/018414, dated May 9, 2019, 11 pages.

* cited by examiner

*Primary Examiner* — Adam C Milligan
(74) *Attorney, Agent, or Firm* — Finnegan, Henderson, Farabow, Garrett & Dunner, LLP

(57) ABSTRACT

Neuroprotective preparations (formulations) employing the synergistic, neurotrophic benefits of nutritional lithium with bioavailable magnesium (FIG. 1). The biological synergism of lithium and magnesium is further enhanced with a proprietary base of synergistic, neurotrophic nutrients. A highly-effective, trans-mucosal, delivery system is included to provide exceptional bioavailability of a palatable, convenient intra-oral preparation, which saturates the vascular tissue in the oral cavity for efficient absorption. Additionally, methods of use are described, allowing for effective, safe, and convenient use of this novel, neuroprotective, antioxidant, anti-inflammatory preparation for humans and animals.

2 Claims, 2 Drawing Sheets

MAGNESIUM/LITHIUM PREPARATIONS FOR NEUROPROTECTION AND NEUROTROPHIC BENEFITS

CROSS-REFERENCE TO RELATED APPLICATIONS

This application represents the U.S. national stage entry of International Application No. PCT/US2019/018414, filed on Feb. 18, 2019, and claims priority to U.S. Provisional Patent Application Ser. No. 62/632,043, filed on Feb. 19, 2018, the disclosures of which are hereby incorporated by reference.

BACKGROUND OF THE INVENTION

Technical Field

This disclosure relates in general to neuroprotective compositions and more particularly to those including preparations of magnesium and lithium.

Background

Neuronal excitotoxicity and the associated increase in free-radical generation and inflammation is a pathophysiological pathway common to a host of primary neurological conditions, neurodegenerative diseases, and secondary neurological conditions leading to diminished cognitive, memory, motor, and sensory function. Some examples of these primary conditions include depression, anxiety, chronic pain, stress intolerance, amyotrophic lateral sclerosis ("ALS"), Parkinson's Disease ("PD"), Alzheimer's Disease ("AD"), and tinnitus. Examples of secondary conditions include traumatic brain injury ("TBI"), exposure to certain neurotoxins, and cerebral ischemia. All of these disease states share a common neurophysiological characteristic: excessive stimulation of post-synaptic neurons (N-methyl D-aspartate receptor mediated; NMDA-R), primarily from the excitatory amino acid neurotransmitters, aspartate and glutamate. Overstimulation of the post-synaptic neuron creates a long-standing partially depolarized state, which opens cell membrane calcium channels, allowing an influx of calcium ions and increasing intracellular calcium concentrations. Calcium is a cofactor for a plethora of intracellular enzymes, including proteases, DNA and RNA endonucleases, and phospholipases. Intracellular hypercalcemia resulting from overstimulation may lead to widespread activation of these enzymes causing destruction of cellular protein, nucleic acids, and membrane structures resulting in apoptosis.

Accordingly, what is needed is a neuroprotective preparation for the prevention and addressment of a wide variety of primary and secondary central nervous system disorders that is highly efficacious, non-toxic, and possesses high-bioavailability (easily absorbable into the systemic circulation), while passing readily across the blood-brain barrier.

SUMMARY OF EMBODIMENTS OF THE INVENTION

Embodiments herein relate to novel, neuroprotective, neurotrophic preparations (formulations). In particular, some embodiments relate to preparations of low-dose, nutritional lithium combined with bioavailable magnesium in a proprietary base of synergistic, neurotrophic nutrients for enhanced therapeutic efficacy (e.g. neuroprotection, neurogenesis, neuroregeneration, antioxidant, anti-inflammatory, aka downregulation of activity). Low-dose, bioavailable lithium is combined with bioavailable magnesium in a proprietary neuroprotective base for highly-efficient oral (e.g. gingival, sublingual, buccal) and gastrointestinal delivery in the prevention and addressment of a wide range of neurological conditions and disorders including cognitive dysfunction and impairment, depression, anxiety, traumatic brain injury, nerve injury, chronic pain, sciatica, attention-deficit disorder, autism, Alzheimer's, Parkinson's, and ALS.

The neuroprotective base comprises a proprietary blend of synergistic nutrients, which enhance lithium and magnesium's neuroprotective and neurotrophic benefits. A highly-effective, oral delivery system is included to provide exceptional bioavailability of a palatable, convenient intra-oral preparation for humans and animals. Additionally, methods of use are described, allowing for effective, safe, and convenient use of a novel, and highly-efficacious, neuroprotective, neurotrophic, antioxidant, anti-inflammatory preparation for general public and clinical use.

The foregoing and other features and advantages of the invention will be apparent to those of ordinary skill in the art from the following more particular description of the invention and the accompanying drawings.

Disclosed herein in some embodiments is a lithium preparation, including magnesium, and a proprietary delivery system. In one embodiment, a neuroprotective preparation comprising elemental lithium; elemental magnesium; and a proprietary neurosupportive blend is disclosed.

In some embodiments, the neuroprotective preparation further comprises a lithium chelate. In some embodiments, the lithium chelate is a salt of orotic acid. In some embodiments, the lithium chelate is a salt of aspartic acid. In some embodiments, the lithium chelate is chosen from the group consisting of succinic acid, gluconic acid, lysinic acid, malic acid, tauric acid, and gluconic acid.

In some embodiments, the neuroprotective preparation further comprises a magnesium chelate. In some embodiments, the magnesium chelating compound is chosen from the group consisting of succinic acid, aspartic acid, lysinic acid, malic acid, tauric acid, citric acid, and gluconic acid. In some embodiments, the magnesium chelating compound is a salt of orotic acid. In some embodiments, the magnesium chelate is a salt of glycine.

In some embodiments, the amount of elemental lithium is between 0.30 and 30 milligrams. In some embodiments, the amount of elemental lithium is between 1.5 and 5.0 milligrams.

In some embodiments, the amount of elemental magnesium is between 50 and 800 milligrams.

Disclosed is a method for providing a neuroprotective treatment (e.g., downregulation of inflammation) to an individual comprising the step of administering a neuroprotective preparation.

In some embodiments, the method further comprises a step assessing risk for a central nervous system disease or condition.

DETAILED DESCRIPTION OF EMBODIMENTS

Figure 1:
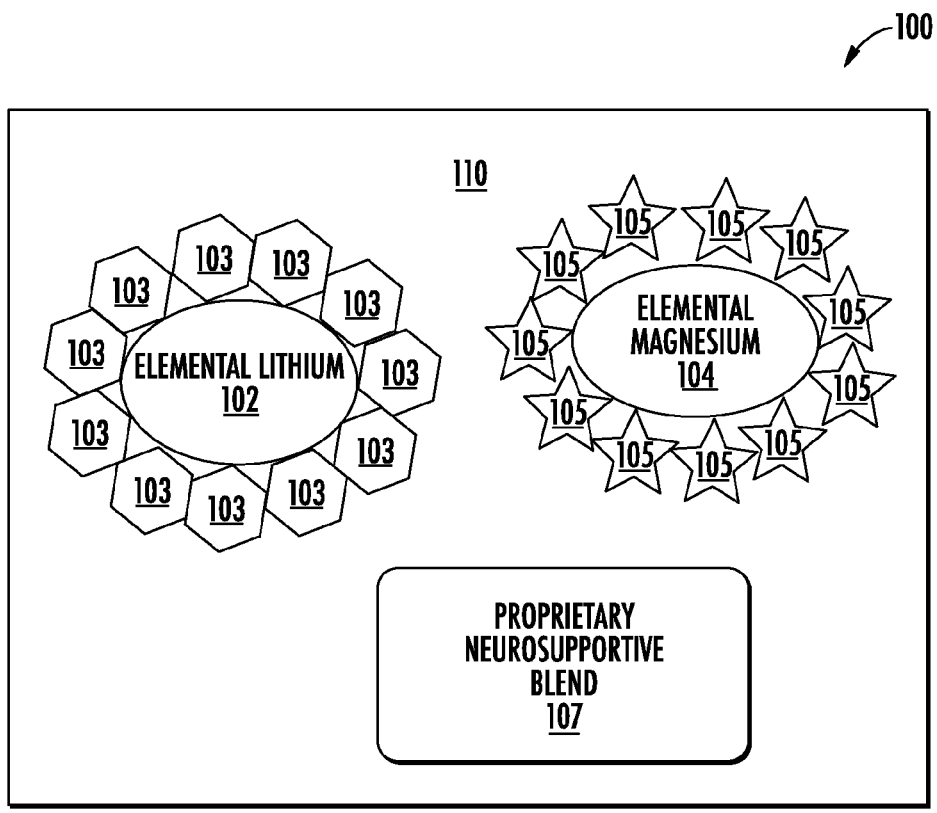
FIG. 1 is a schematic representation of a neuroprotective preparation.

As discussed above, the disclosed embodiments relate to preparations of low-dose readily absorbable lithium, in combination with magnesium and in some embodiments a proprietary neurosupportive blend, for oral administration and oro-gingival-buccal absorption as a central nervous system neuro-protectant and methods of use.

A wide range of primary central neurological diseases and secondary conditions manifest cognitive, memory, motor, and sensory impairment as primary and debilitating symptoms. A few non-limiting examples of such diseases and conditions are listed herein above and include amyotrophic lateral sclerosis ("ALD"), Parkinson's Disease ("PD"), Alzheimer's Disease ("AD"), post-traumatic stress disorder ("PTSD"), attention deficit hyperactivity disorder ("ADHD"), depression/anxiety, and tinnitus. Examples of secondary conditions include traumatic brain injury ("TBI"), chronic post-traumatic or post-surgical neuropathic pain, acute or chronic exposure to certain toxins, for example mercury and ethanol; and cerebral ischemia.

Although, used as a drug for nearly 70 years, lithium's true nature is that of a nutrient required for a number of essential biological processes including nutrient utilization, neuromodulation and neuroprotection, antioxidant defenses, Nrf2 pathway activation (via GSK3 inhibition), stem cell proliferation and mobilization, and neural growth factor stimulation. The effects and mechanism of action of lithium when used in high doses as a pharmaceutical agent for mania and a broad variety of other central nervous system disorders, however, remain incompletely understood. In high doses, lithium acts as a drug. In smaller doses, however, lithium acts as a nutrient. Lithium is active in vitamin B12 and folate mucosal transport, regulation of inflammation and prostaglandin biosynthesis, hormonal regulation and reproductive processes, neural growth factor production (e.g. brain-derived neurotrophic factor; BDNF), neuromodulation, and neuroprotection. Lithium competes for cell surface receptors in neurons and a variety of other tissues which bind magnesium, and as a "companion nutrient", augments the effects of magnesium.

While not intending to limit the disclosure herein to a particular mechanism or mechanisms, there is evidence that lithium is trophic for a variety of cell lines, including neurons, and granulocytes, possibly through complex mechanisms inducing propagation and differentiation of pluripotent stem cells. Lithium stimulates proliferation of stem cells, including bone marrow and neural stem cells in the subventricular zone, striatum, and forebrain. The stimulation of endogenous neural stem cells may explain why lithium increases brain neuronal volume and density in those receiving chronic lithium therapy. Indeed, bipolar patients on chronic, high-dose lithium therapy have higher brain volumes then similar cohorts of untreated patients. Lithium acts as an indirect antioxidant by preventing excessive free-radical production from NMDA receptor hyperactivity and by inducing increased activity of endogenous antioxidant enzyme systems via GSK3 inhibition/Nrf2 activation. In animals, lithium upregulates neurotrophins, including brain-derived neurotrophic factor (BDNF), nerve growth factor, neurotrophin-3 (NT3), as well as receptors to these growth factors in brain. Some populations wherein chronic ingestion of increased amounts of lithium through drinking water demonstrate reductions in all-cause mortality.

A possible mechanism of action for the neuroprotective effects of lithium is through to be inhibition of the N-methyl-D-aspartate receptor ("NMDA"), with which magnesium and/or lithium interact as a receptor ligand, on post-synaptic cortical neurons of the central nervous system. NMDA receptors are ubiquitous throughout the brain and play a role in regulation of the excitatory state of post-synaptic neurons. NMDA receptors act as a cationic membrane "pore," primarily for calcium ions although other cations such as sodium, zinc, and protons may pass into the cell. In conditions wherein the post-synaptic neuron is polarized and glutamate is absent from the synapse, a local negative membrane charge permits the pore to be blocked with a magnesium ion. Under conditions wherein 1) glutamate is present within the synapse at a sufficient concentration; and 2) the post-synaptic neuron is partially depolarized creating a neutral or relative positive membrane charge, the magnesium ion is displaced, the pore opens, and calcium ions are allowed to pass freely through the NMDA receptor into the cell. Once intracellular, calcium exerts a myriad of secondary effects, largely through its role as a secondary messenger and enzyme cofactor. Increased intracellular calcium leads to increased cellular enzyme activity of proteases, nucleases, and phospholipases, breaking down structural components and functional machinery of the cell and often leading to cell death.

Keeping the baseline state of the NMDA receptor pore in a closed configuration, therefore, is important for the proper function and survival of a post-synaptic neuron. There are at least two potential sites of action to keep the receptor pore closed to influx of calcium and other cations into the neuron: 1) adequate-to-high synaptic magnesium concentrations; and 2) inhibition of tyrosine kinase-mediated phosphorylation of the NR2B receptor subunit.

Given a polarized or neutral post-synaptic cell membrane, in combination with adequate extracellular magnesium concentrations, magnesium binds to the receptor pore and blocks influx of calcium.

Several physiologic mechanisms resist a partially depolarized state in the post-synaptic cell membrane, keeping the pore closed to the influx of calcium an enhancing appropriate NMDA receptor function. One of these potentiating mechanisms is tyrosine-mediated phosphorylation of the NMDA receptor subunits, tending to "close" the receptor pore by causing an amphoteric shift in one or more protein subunits. Tyrosine phosphatase-mediated NR2B subunit phosphorylation potentiated by the lithium cation has been shown to cause depression of NMDA receptor currents. The present invention seeks to militate against activation of a final common pathway for neuronal cell injury and death—elevated intracellular calcium levels—by impeding permeability of the NMDA receptor to calcium.

Unabated oxidative stress due to suboptimal, deficient intake of specific antioxidant nutrients (e.g. magnesium, lithium, zinc) coupled with neuronal excitotoxicity and the associated increase in free-radical generation and inflammation is a pathophysiological pathway common to a host of primary neurological conditions, neurodegenerative diseases, and secondary neurological conditions leading to diminished cognitive, memory, motor, and sensory function. Some examples of these primary conditions include depression, anxiety, sleep disturbances, chronic pain, sensitivity to stress, and chronic inflammation. Examples of secondary conditions include traumatic brain injury ("TBI"), exposure to certain neurotoxins, and cerebral ischemia. All of these disease states share the following common physiological characteristics: oxidative stress from excessive unabated free-radical generation, elevated inflammatory biomarkers (e.g. hsCRP), excessive stimulation of post-synaptic neurons (N-methyl-D-aspartate receptor mediated; NMDA-R), primarily from the excitatory amino acid neurotransmitters, aspartate and glutamate, and chronic inflammation. Magnesium, lithium, and zinc deficiencies contribute to elevated inflammatory biomarkers, compromised antioxidant defenses via reduced Nrf2 pathway activation, NMDA receptor hyperactivity, and to the overstimulation of the post-synaptic neuron leading to a long-standing partially depolarized state, which opens cell membrane calcium channels, allowing an influx of calcium ions and increasing intracellular calcium concentrations. Calcium is a cofactor for a plethora of intracellular enzymes, including proteases, DNA and RNA endonucleases, and phospholipases. Intracellular hypercalcemia resulting from overstimulation may lead to widespread activation of these enzymes causing destruction of cellular proteins, nucleic acids, and membrane structures resulting in eventual neuronal death.

Magnesium and lithium possess a special relationship in chemistry, known as a "diagonal relationship" on the Periodic Table of Elements resulting in the two elements having more chemical and physical properties in common than the other elements in their respective groups. This can lead to a synergism between the two elements and improves each element's therapeutic efficacy at low doses (e.g. ≤400 for Mg; ≤20 mg for Li). Magnesium and lithium serve important neuroprotective and neurotrophic functions in the center nervous system, and act as a "protective shield" against biologically damaging excitotoxins such as lead, mercury, and cadmium. Chronic stress, excess sweating, sugar, caffeine, alcohol, calcium supplementation, and mineral antagonists such as glyphosate and fluoride in our food and water increase the nutritional requirements for these elements (and others). Those who are under chronic stress, or have experienced a recent trauma or injury, would especially benefit from additional amounts of these nutrients, as greater amounts are loss (and required) during physical, emotional, and psychological stress.

An optimal, therapeutic neuroprotective intervention to prevent and/or treat unabated oxidative stress and post-synaptic overstimulation would ideally create a microenvironment wherein oxidative stress is reduced and the depolarization threshold for opening calcium channels in the cell membranes of neurons is increased. Additionally, the therapeutic must be convenient for use in humans and animals—and easy to take—making a "soft-chew", "gummy", lozenge, chewable tablet, water soluble powder in packet form, "food-form," partially orally-absorbable preparation greatly advantageous. Tablet and capsule forms of the neuroprotective preparation (formulation) will also be provided, and will provide similar benefits with a slower onset of therapeutic effects.

FIG. 1 is a schematic representation of a neuroprotective preparation 100. schematic representation of a neuroprotective preparation 100. FIG. 1 shows neuroprotective preparation 100 comprising an elemental lithium 102, an elemental magnesium 104, a lithium chelating compound 103, a magnesium chelating compound 105, and a proprietary neurosupportive blend 107 all within a delivery system 110. Nonetheless, the compositions described herein may include fewer or more constituents than those illustrated in FIG. 1.

Elemental lithium 102 has multiple beneficial effects. With respect to NMDA receptor inhibition, elemental lithium 102 is included as a component of neuroprotective preparation 100 because lithium is thought to protect against glutamate-induced excitotoxicity in neurons by decreasing NR2B subunit tyrosine phosphorylation. Experimental evidence suggests effects are significant at extracellular concentrations of 0.1-0.2 mM, with nearly complete protection seen at levels of 1.0 mM. These concentrations are in the order of one-tenth the extracellular intracerebral concentrations of elemental lithium routinely achieved in the treatment of bipolar disorder. Given the daily dose of lithium used in treating bipolar disorder is approximately 1,800 milligrams per day (containing 340 mg of elemental lithium), the exact dose being dependent on a variety of individual factors, the anticipated daily dose of elemental lithium for use in providing a neuroprotective treatment is 5 to 180 milligrams of elemental lithium per day. Accordingly, neuroprotective preparation comprises a concentration of elemental lithium 102 in the range of approximately 1.0 to 20.0 milligrams per tablet with a plurality of tablets administered in two to three divided doses, in some embodiments.

FIG. 1 also shows lithium chelating compound 103. Intestinal and trans-mucosal absorption of lithium, and other mineral nutrients such as magnesium, is increased by a chelate. In some embodiments, lithium chelating compound 103 is a salt of orotic acid. In some embodiments, lithium chelating compound 103 is a salt of succinic acid, aspartic acid, gluconic acid, lysinic acid, malic acid, tauric acid, or citric acid. It is anticipated that as experimentation and research in the art of enhanced trans-mucosal lithium absorption progresses, other chelating compounds may be used as lithium chelating compound 103, in some embodiments.

Similarly, FIG. 1 also shows elemental magnesium 104 and magnesium chelating compound 105. Magnesium concentrations in a neuronal synapse are necessary to saturate the post-synaptic population of NMDA receptors, therein keeping the receptor pores closed to the influx of extracellular calcium ions when the post-synaptic neuron is in a partially polarized state. Hypomagnesaemia is associated with a plethora of symptomatic neurological abnormalities, such as depression, anxiety, chronic fatigue, sleep disturbances, hyperreflexia, tremor, confusion, hallucinations, convulsions, hyperacusis, nystagmus, tetany, delirium tremens, and extrapyramidal disorders. The beneficial neurological effects of both magnesium and lithium are thought to augment one another, such that lithium supplementation increases the effects of magnesium in a manner which is greater than cumulative, and vice-versa. Therefore, by including both elemental magnesium 104 and elemental lithium 102, each in a highly-absorbable chelated form in neuroprotective preparation 100, lower doses of both elemental magnesium 104 and elemental lithium 102 will be necessary to achieve the desired end effect. Lower doses of elemental magnesium 104 and elemental lithium 102 are less likely to cause undesired side-effects or toxicities, thereby increasing the safety of neuroprotective preparation 100.

Like lithium, trans-mucosal absorption of elemental magnesium is greatly increased by combining elemental magnesium with an organic chelate (e.g. glycinate). Accordingly, neuroprotective preparation 100 comprises magnesium chelating compound 105, as shown in FIG. 1. In some embodiments, magnesium chelating compound 105 is a salt of the amino acid glycine. In some embodiments, magnesium chelating compound 105 is a salt of succinic acid, aspartic acid, gluconic acid, lysinic acid, malic acid, tauric acid, orotic acid, or citric acid. It is anticipated that as experimentation and research in the art of enhanced trans-mucosal magnesium absorption progresses, other chelating compounds may be used as lithium chelating compound 105, in some embodiments.

The total concentration of elemental magnesium 104 per dose of neuroprotective compound 100 is calculated to provide adequate intracerebral levels of magnesium without being so high as to increase the risk of toxicity from hypermagnesemia. Accordingly, the amount of elemental magnesium 104, in some embodiments, is between approximately 50 milligrams and 800 milligrams.

Proprietary neurosupportive blend 107, in some embodiments, is a commercially available blend of vitamins, minerals, and other nutrients compounded to promote neurological and general health. In some embodiments, proprietary neurosupportive blend 107 comprises, per chewable tablet, soft chew, gummy, lozenge, tablet, capsule, or packet: kelp, 25-100 mg; Extramel French melon extract, 0.5-10 mg; vitamin B1, 1-20 mg; vitamin B2, 1-20 mg; vitamin B6, 1-20 mg; Vitamin B3, 5-50 mg; vitamin B5, 5-50 mg; Vitamin B12, 50-1,000 mcg; Biotin, 30-300 mcg; PABA, 0.50-10 mg; vitamin C, 50-500 mg; vitamin D, 400-2,000 IU; natural vitamin E, 15-200 iu; boron (glycinate), 0.250-5 mg; zinc (glycinate), 2-15 mg; manganese (glycinate), 0.5-5 mg; selenium (e.g. glycinate), 50-200 mcg; molybdenum (glycinate), 50-200 mcg; and chromium (nicotinate glycinate or polynicotinate), 50-200 mcg. The foregoing is by way of example only; other formulations of proprietary neurosupportive blend 107 are possible. Additionally, it is anticipated that as scientific investigation generates additional data regarding the role of the various compounds comprising proprietary neurosupportive blend 107 are generated, the composition of proprietary neurosupportive blend 107 will change accordingly.

FIG. 1 shows delivery system 110 for trans-mucosal absorption and optimal intracerebral concentration of elemental lithium 102, elemental magnesium 104, and active elements of proprietary neurosupportive blend 107. Delivery system 100, in some embodiments, is a specialized combination of the highly-bioavailable nutrients, such as Albion® minerals (e.g. glycinates), or orotates (e.g. lithium); naturally occurring folate (e.g. folinic acid), naturally occurring vitamin B12 (e.g. methylcobalamin); kelp (a rich source of iodine and trace minerals); French melon extract, (naturally occurring source of superoxide dismutase and catalase) along with non-GMO tableting agents and excipients, which facilitate oral bioavailability through rapid dissolution and mucosal absorption from within the oral cavity. Some non-limiting examples of such excipient compounds include xylitol, cellulose, silicon dioxide, citric acid, organic stevia (leaf) extract, monk fruit extract, and natural flavors. Other such compounds as are known in the art of oral drug absorption and delivery systems may be used in some embodiments. In these and some other embodiments, neuroprotective preparation 100 is taken as a tablet, capsule, chewable wafer, soft chew, gummy, or lozenge placed in the mouth. In some embodiments, the soft chew, gummy, or lozenge is held under the tongue, chewed, or placed in a buccal recess and allowed to dissolve. In some embodiments, the soft chew or gummy is chewed and swallowed.

Figure 2:
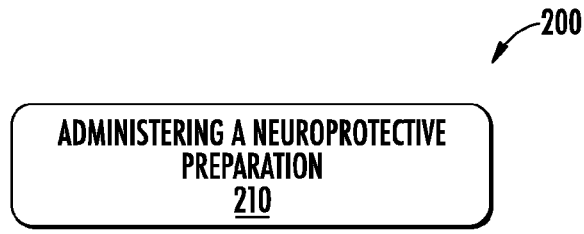
FIG. 2 is a flowchart showing steps of a method 200 for using a neuroprotective preparation.

FIG. 2 shows a flowchart showing steps of a method 200 for using a neuroprotective preparation. As shown by FIG. 2, step 210, is administering a neuroprotective preparation. Administering step 210 comprises prescribing and/or providing instructions for consumption of a neuroprotective preparation. In some embodiments, administering step 210 is prescribing a soft chew, gummy, or lozenge to be dissolved under the tongue, in the buccal space, or elsewhere in the oral cavity one or more times each day. In some embodiments, the soft chew, gummy, or lozenge is a chewable mass which is chewed before swallowing. In some embodiments, administering step 210 is prescribing a non-chewable tablet which the user swallows. In some embodiments, the neuroprotective preparation is a liquid preparation which the user swallows. In some embodiments, the neuroprotective preparation is a liquid solution which is administered intravenously to the user. In some embodiments, the neuroprotective preparation is a liquid solution or suspension which is administered to the user through a feeding tube, such as a naso-enteric feeding tube or a gastrostomy feeding tube, for example.

Figure 3:
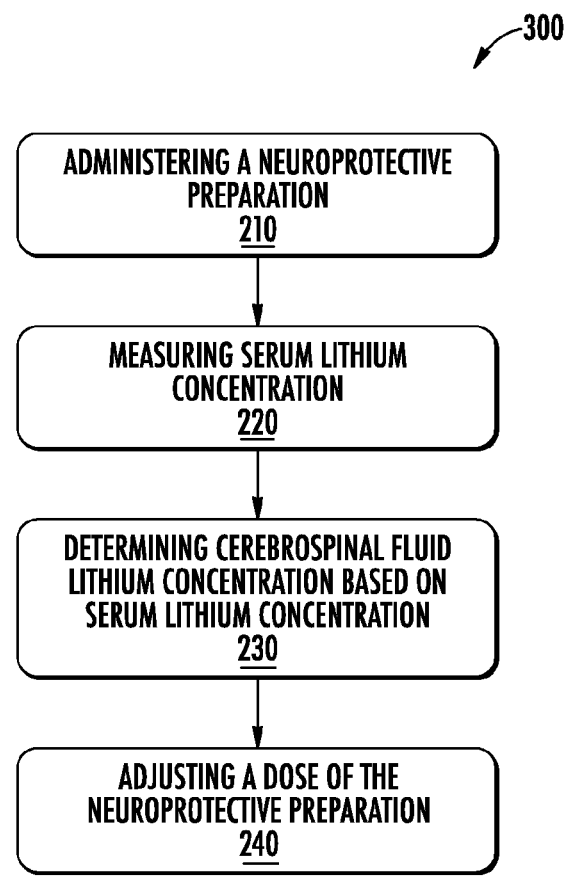
FIG. 3 is a flowchart showing steps of a method 300 for treating a person at risk for a degenerative neurologic condition with a neuroprotective preparation.

FIG. 3 shows a flowchart showing steps of a method 300 for using a neuroprotective preparation. Method 300, in some embodiments, comprises an administering step 310, a measuring step 320, a determining step 330, and an adjusting step 340. Administering step 310 is a step administering a neuroprotective preparation.

The remaining steps of method 300 address determining an effective but safe dose of lithium during a period of neuroprotective preparation therapy by measuring serum lithium levels, extrapolating this measurement to predict the lithium level within the cerebrospinal fluid, and adjusting the dose of the neuroprotective preparation up or down accordingly. Measuring step 320 comprises measuring a serum lithium concentration. Methods of measuring the concentration of elemental lithium within human serum are widely known in the art. After the serum lithium concentration is known, determining step 330, comprising determining the cerebrospinal fluid lithium concentration based on the serum lithium concentration, is performed.

Although variability between individuals is present, particularly in certain disease states such as hepatic or renal insufficiency or failure, the concentration of lithium within cerebrospinal fluid is directly dependent upon the serum lithium concentration and can be estimated by extrapolation from dose serum concentration curves known in the art and available to practitioners using lithium therapy. In disease states or other circumstances wherein knowing the cerebrospinal fluid concentration of lithium is critical, such as may exist in a critically ill human patient with complex pathophysiology, determining step 330 comprises taking a direct measurement of lithium concentration from a sample of cerebrospinal fluid. Cerebrospinal fluid for performance of a laboratory lithium assay (techniques of which are widely commercially available and known in the art) is obtained by conventional clinical methods, such as lumbar puncture. Adjusting step 340 comprises adjusting a dose of the neuroprotective preparation. Adjusting step 340 is performed using the results of determining step 330, comprising a cerebrospinal lithium level obtained by either extrapolation or direct measurement as described herein above. The dose of neuroprotective preparation is increased, decreased, or left unchanged accordingly to achieve the desired cerebrospinal fluid lithium level for the level of neuroprotective therapy desired, based upon the presence or absence of neurological diseases or conditions, and any individual risk factors present therefor, based evidence-based best practices.

A neuroprotective preparation and method of use has been described. The biological synergism of lithium and magnesium are utilized to create an optimal therapeutic effect at low, but nutritionally significant cerebrospinal fluid lithium levels in order to minimize (and effectively avoid) toxicity and the risk of undesirable side effects of low-dose lithium therapy.

The neuroprotective preparation also may comprise a proprietary neurosupportive blend of synergistic nutrients for maximum therapeutic efficacy. An excipient delivery system to provide bioavailability of a palatable, convenient intra-oral preparation is included. Additionally, methods of use are described, allowing for effective, safe, and convenient use of this novel, highly-bioavailable, nontoxic, magnesium/lithium formulation for humans and animals, in either a clinical or non-clinical setting.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above.

I claim:

1. A composition consisting of lithium orotate or lithium glycinate, in an amount of 1-10 milligrams; magnesium taurate and magnesium malate, wherein the combination of magnesium taurate and magnesium malate is provided in an amount of 100-400 milligrams; 25-100 mg of kelp; 0.5-10 mg of French melon extract; 1-20 mg of vitamin B1; 1-20 mg of vitamin B2; 1-20 mg of vitamin B6; 5-50 mg of vitamin B3; 5-50 mg of vitamin B5; 50-1,000 mcg of vitamin B12; 30-300 mcg of biotin; 0.50-10 mg of para-aminobenzoic acid (PABA); 50-500 mg of vitamin C; 400-2,000 iu of vitamin D; 15-200 iu of natural vitamin E; 0.250-5 mg of boron glycinate; 2-15 mg of zinc glycinate; 0.5-5 mg of manganese glycinate; 50-200 mcg of selenium glycinate; 50-200 mcg of molybdenum glycinate; and 50-200 mcg of chromium nicotinate glycinate or polynicotinate.

2. A composition consisting of lithium orotate or lithium glycinate, in an amount of 1-10 milligrams; magnesium taurate and magnesium malate, wherein the combination of magnesium taurate and magnesium malate is provided in an amount of 100-400 milligrams; 25-100 mg of kelp; 0.5-10 mg of French melon extract; 1-20 mg of vitamin B1; 1-20 mg of vitamin B2; 1-20 mg of vitamin B6; 5-50 mg of vitamin B3; 5-50 mg of vitamin B5; 50-1,000 mcg of vitamin B12; 30-300 mcg of biotin; 0.50-10 mg of para-aminobenzoic acid (PABA); 50-500 mg of vitamin C; 400-2,000 iu of vitamin D; 15-200 iu of natural vitamin E; 0.250-5 mg of boron glycinate; 2-15 mg of zinc glycinate; 0.5-5 mg of manganese glycinate; 50-200 mcg of selenium glycinate; 50-200 mcg of molybdenum glycinate; 50-200 mcg of chromium nicotinate glycinate or polynicotinate; tapioca syrup; raw cane sugar; palm oil; natural flavors; beet juice; sunflower lecithin; and salt.

* * * * *